United States Patent [19]

Arai et al.

[11] Patent Number: 5,180,825
[45] Date of Patent: Jan. 19, 1993

[54] MITOMYCIN DERIVATIVES

[75] Inventors: Hitoshi Arai; Motomichi Kono, both of Shizuoka; Masaji Kasai, Fujisawa; Katsushige Gomi, Susono; Tadashi Ashizawa, Numazu, all of Japan

[73] Assignee: Kyowa Hakko Kogyo Co., Ltd., Tokyo, Japan

[21] Appl. No.: 791,188

[22] Filed: Nov. 13, 1991

[30] Foreign Application Priority Data

Nov. 13, 1990 [JP] Japan .................. 2-306663

[51] Int. Cl.$^5$ .................. C07D 239/02; C07D 401/00; C07D 417/00; C07D 403/00; C07D 487/00; C07D 487/14
[52] U.S. Cl. ............................. 544/318; 544/230; 544/298; 544/315; 544/318; 546/15; 546/271; 548/125; 548/147; 548/181; 548/182; 548/183; 548/216; 548/217; 548/221; 548/263.2; 548/263.4; 548/263.6; 548/264.2; 548/264.4; 548/407; 548/411; 548/422; 548/311.7; 548/301.1; 548/305.1; 548/357.5; 548/364.7

[58] Field of Search ............... 544/298, 315, 318, 319, 544/230; 546/271, 15; 548/159, 181–183, 264.2, 264.4, 422, 147, 216, 407, 411, 263.2, 263.4, 263.6, 186, 125, 217, 221, 337–339

[56] References Cited

U.S. PATENT DOCUMENTS

| | | | |
|---|---|---|---|
| 4,863,935 | 9/1989 | Shida et al. | 548/422 |
| 4,880,825 | 11/1989 | Kasai et al. | 548/422 |
| 4,888,341 | 12/1989 | Remers et al. | 548/422 |
| 5,023,253 | 6/1991 | Remers et al. | 548/422 |
| 5,068,349 | 11/1991 | Kanda et al. | 548/422 |
| 5,091,523 | 2/1992 | Talebian et al. | 548/422 |

FOREIGN PATENT DOCUMENTS

| | | |
|---|---|---|
| 307179 | 3/1989 | European Pat. Off. . |
| 359480 | 3/1990 | European Pat. Off. . |
| 9001931 | 3/1990 | PCT Int'l Appl. . |
| 2134514 | 8/1984 | United Kingdom . |

*Primary Examiner*—Cecilia Tsang
*Attorney, Agent, or Firm*—Antonelli, Terry Stout & Kraus

[57] ABSTRACT

Disclosed in a mitomycin derivative represented by the formula (I): t,10 wherein W is a heterocyclic group.

19 Claims, No Drawings

MITOMYCIN DERIVATIVES

BACKGROUND OF THE INVENTION

The present invention relates to novel mitomycin derivatives having antitumor and antibacterial activities.

Mitomycins are known as antibiotics having, in general, antibacterial and antitumor activities. Among known mitomycin derivatives, are those where one hydrogen in the methyl group at the 6-position is substituted by deuterium ($^2H$) or tritium ($^3H$), as disclosed in EP-0307179A3, and those where one hydrogen in the methyl group at the 6-position is substituted by alkoxy or alkylthio, as disclosed in EP-0359480A1, and represented by the following formula:

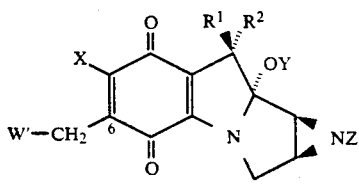

in which W' represents alkoxy or alkylthio.

The term "JP-A" as referred to herein means "Japanese Published Unexamined Patent Application".

SUMMARY OF THE INVENTION

The object of the present invention is to provide novel mitomycin derivatives in which the 6-position is substituted by heterocyclicthiomethyl groups.

The present invention relates to mitomycin derivatives represented by the formula (I):

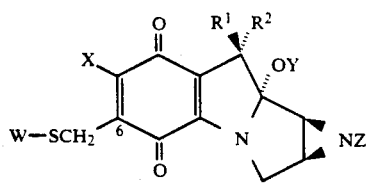 (I)

where W represents a member selected from the groups (a), (b), (c), (d), and (e):

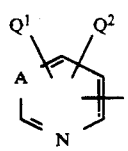 (a)

wherein A is —N= or —CR$^3$= wherein R$^3$ is selected from hydrogen, hydroxy, amino, aryl, and C1-6 alkyl, Q$^1$ and Q$^2$ are each independently selected from hydrogen, hydroxy, amino, aryl and C1-6 alkyl,

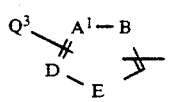 (b)

wherein A$^1$ has the same meaning as A, Q$^3$ has the same meaning as Q$^1$, B and D are each independently selected from —N= and —CR$^4$= wherein R$^4$ has the same meaning as R$^3$, E is selected from S, O and NR$^5$ wherein R$^5$ has the same meaning as R$^3$,

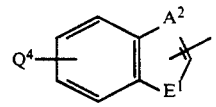 (c)

wherein A$^2$ has the same meaning as A, E$^1$ has the same meaning and E and Q$^4$ has the same meaning as Q$^1$,

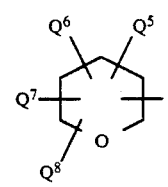 (d)

wherein Q$^5$, Q$^6$, Q$^7$ and Q$^8$ are each independently selected from hydrogen, hydroxy, C1-6 alkanoyloxy, hydroxymethyl and C1-6 alkanoyloxymethyl, and

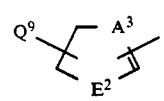 (e)

wherein A$^3$ has the same meaning as A, E$^2$ has the same meaning as E, Q$^9$ has the same meaning as Q$^1$, X is selected from methoxy and amino, Y is selected from hydrogen and methyl, Z is selected from hydrogen, methyl and C1-6 alkanoyl, and one of R$^1$ and R$^2$ represents carbamoyloxymethyl, and the other represents hydrogen or R$^1$ and R$^2$ are combined to form methylene.

DETAILED DESCRIPTION OF THE INVENTION

The compound represented by formula (I) is referred to as Compound (I); and hereunder the same shall apply to other compounds of other formulae.

In the definitions of respective groups in formula (I), the C1-6 alkyl refers to straight or branched alkyl, and includes, for example, methyl, ethyl, propyl, isopropyl, butyl, isobutyl, sec-butyl, tert-butyl, pentyl, neopentyl, hexyl, etc. The C1-6 alkanoyl and the alkanoyl moiety in the C1-6 alkanoyloxy group and the C1-6 alkanoyloxymethyl group include, for example, formyl, acetyl, propionyl, butyryl, isobutyryl, pivaloyl, valeryl, isovaleryl, etc.

Methods of preparing Compounds (I) are mentioned below.

Preparation Method 1

Compound (Ia), which is Compound (I) where X is amino and Compound (Ib), which is Compound (I) where X is methoxy, are produced by the following reaction steps:

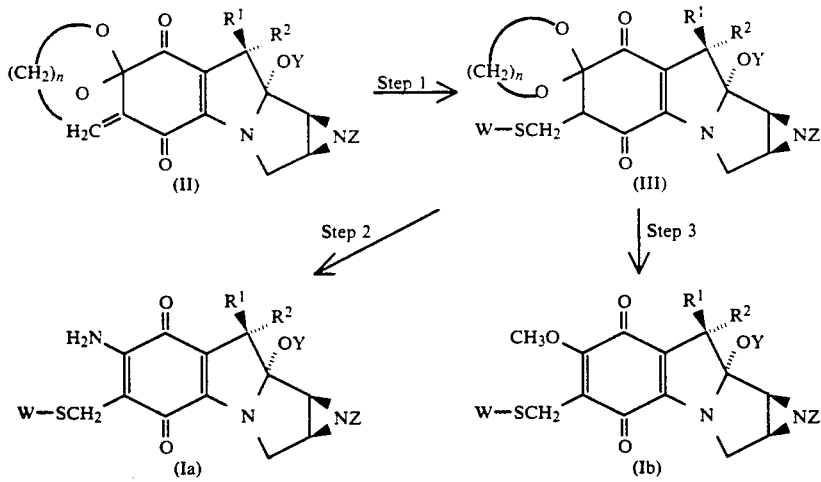

wherein n represents an integer of 2 and 3; and W, Y, Z, R[1] and R[2] have the same meanings as described above.

Step 1

Compound (III) can be prepared by reacting Compound (II) with WSH (wherein W has the same meanings as described above) in an inert solvent, if necessary, in the presence of a base.

As the solvent used in the reaction, mention may be made of ether, tetrahydrofuran, dichloromethane, chloroform, dimethylformamide (DMF) singly or in combination.

As the base used for the reaction, mention may be made of organic bases such as pyridine and triethylamine.

The reaction is generally carried out at a temperature of 0° to 30° C. and completed in 10 minutes to 24 hours.

Compound (II) which is a starting material is a known compound described in JP-A-6275/89 and JP-A-70490/89.

Step 2

Compound (Ia), which is Compounds (I) where X is $NH_2$, is prepared by reacting Compound (III) with ammonia or ammonium acetate in an inert solvent.

Any solvent can be used so long as it is inert to the reaction and Compound (III) is dissolved in the solvent. As the solvent, alcohols such as methanol, ethanol; ethers such as ether, tetrahydrofuran; halogenated alkanes such as dichloromethane, chloroform; acetonitrile, DMF, dimethylsulfoxide, may be used singly or in combination.

The reaction is generally carried out at a temperature of 0° to 30° C. and completed in one hour to 14 days.

Step 3

Compound (Ib), which is Compounds (I) where X is $CH_3O$, is prepared by reacting Compound (III) with methanol in the presence of a base.

As the base used in the reaction, mention may be made of alkoxides, hydroxides, carbonates or bicarbonates of alkali metals or alkaline earth metals, tertiary amines or quaternary ammonium hydroxides. The base is used in an amount of 0.001 to 10 equivalents, preferably in an amount of 0.01 to 3 equivalents, based on Compound (III).

The reaction is carried out at a temperature of 0° to 30° C. and completed in one to 24 hours.

In Steps 2 and 3, Compound (III) wherein Z is C1-6 alkanoyl is simultaneously deacylated under the above-mentioned reaction conditions to give the corresponding Compounds (Ia) and (Ib) where Z is hydrogen.

The intermediates and the products to be produced in the above-mentioned preparation method can be isolated and purified by using various conventional purification methods which are generally employed in organic synthetic chemistry, for example, by neutralization, filtration, extraction, washing, drying, concentration, recrystallization and various chromatographies. In the case of the intermediates, they can be applied directly to the next step without further purification. Compounds (I) may be obtained in the form of adducts with water or various solvents, which are also within the scope of the present invention.

Specific examples of Compounds (I) obtained by the above-mentioned processes are shown in Table 1 below.

TABLE 1
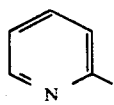
| Compound (Example) | W | X | Y | Z | R$^1$ | R$^2$ |
|---|---|---|---|---|---|---|
| 1 (1) | 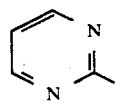 | NH$_2$ | CH$_3$ | H | CH$_2$OCONH$_2$ | H |
| 2 (2) | 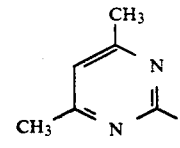 | NH$_2$ | CH$_3$ | H | CH$_2$OCONH$_2$ | H |
| 3 (3) | 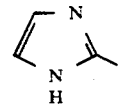 | NH$_2$ | CH$_3$ | H | CH$_2$OCONH$_2$ | H |
| 4 (4) | 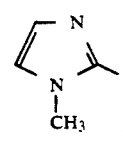 | NH$_2$ | CH$_3$ | H | CH$_2$OCONH$_2$ | H |
| 5 (5) | 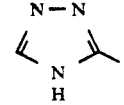 | NH$_2$ | CH$_3$ | H | CH$_2$OCONH$_2$ | H |
| 6 (6) | 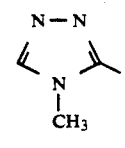 | NH$_2$ | CH$_3$ | H | CH$_2$OCONH$_2$ | H |
| 7 (7) | 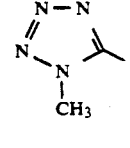 | NH$_2$ | CH$_3$ | H | CH$_2$OCONH$_2$ | H |
| 8 (8) | 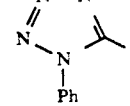 | NH$_2$ | CH$_3$ | H | CH$_2$OCONH$_2$ | H |
| 9 (9) |  | NH$_2$ | CH$_3$ | H | CH$_2$OCONH$_2$ | H |
| 10 (10) |  | NH$_2$ | CH$_3$ | H | CH$_2$OCONH$_2$ | H |

TABLE 1-continued

[Structure: quinone ring with substituents X, O, R¹, R², OY, W-SCH₂, and fused N-containing ring with NZ]

| Compound (Example) | W | X | Y | Z | R¹ | R² |
|---|---|---|---|---|---|---|
| 11 (11) | [thiazoline with N, S ring] | NH₂ | CH₃ | H | CH₂OCONH₂ | H |
| 12 (12) | [thiazole-type N, S ring] | NH₂ | CH₃ | H | CH₂OCONH₂ | H |
| 13 (13) | [benzothiazole] | NH₂ | CH₃ | H | CH₂OCONH₂ | H |
| 14 (14) | [CH₃-substituted N-N, S ring (thiadiazole)] | NH₂ | CH₃ | H | CH₂OCONH₂ | H |
| 15 (15) | [benzoxazole] | NH₂ | CH₃ | H | CH₂OCONH₂ | H |
| 16 (16) | [tetraacetylated sugar: CH₂OAc, AcO, AcO, OAc, O] | NH₂ | CH₃ | H | CH₂OCONH₂ | H |
| 17 (17) | [sugar: CH₂OH, HO, HO, OH, O] | NH₂ | CH₃ | H | CH₂OCONH₂ | H |
| 18 (18) | [thiophene, S ring] | NH₂ | CH₃ | H | CH₂OCONH₂ | H |

The anti-tumor activity and acute toxicity of typical examples of Compound (I) are described below.

Growth Inhibition Test on HeLa S₃ Cells

HeLa $S_3$ cells were suspended in a MEM medium containing 10% fetal calf serum and 2 mM glutamine at a concentration of $3 \times 10^4$ cells/ml, and 0.1 ml of the cell suspension was put into each well of a 96-well microtiter plate.

After culturing at 37° C. overnight in a carbon dioxide gas incubator, 0.05 ml of a test sample appropriately diluted with the medium was added to each well. The cells were further cultured for one hour in the carbon dioxide gas incubator and the culture supernatant was removed. The residue was washed once with a phosphate buffer saline [PBS(−)] and 0.1 ml of a fresh medium was added to each well, and the cells were further incubated at 37° C. for 72 hours in the carbon dioxide gas incubator. After removal of the supernatant, 0.1 ml of a culture medium containing 0.02% Neutral Red was added to each well, and the cells were further incubated at 37° C. for one hour in the carbon dioxide gas incubator to stain the cells. After removal of the culture supernatant, each well was washed once with a physiological saline, and the dye was extracted with 0.001 N HCl/30% methanol. Absorbance of the extract at 550 nm was measured with a microplate reader. The cell growth inhibition percentage was calculated according to the following formula from the absorbance of the extract of the cells treated with the test compound in various concentrations and that of intact cells.

Cell Growth Inhibition Percentage (%) = 100 −

$$\frac{(\text{Absorbance of cells treated with test compound}) - (\text{Absorbance of cell-free well})}{(\text{absorbance of intact cells}) - (\text{absorbance of cell-free well})} \times 100$$

From the cell growth inhibition percentage thus obtained, the concentration of the test compound which inhibits cell growth by 50% ($IC_{50}$) was determined. The results are shown in Table 2.

TABLE 2

| Test Compound | $IC_{50}$ ($\mu M$) |
| --- | --- |
| 1 | 1.8 |
| 2 | 0.19 |
| 3 | 0.95 |
| 4 | 1.1 |
| 11 | 0.82 |
| 12 | 1.4 |
| 13 | 0.70 |
| 16 | 1.1 |

Test Example 2

Anti-tumor Activity to Sarcoma 180 Solid Tumor $5 \times 10^6$ Sarcoma 180 cells were abdominally implanted into a ddY mouse and the cells were collected from the ascites of the mouse 7 days after the implantation. The cells were washed once with a sterilized physiological saline solution and then suspended in a sterilized physiological saline solution to prepare a cell suspension of $5 \times 10^7$ cells/ml. 0.1 ml of the cell suspension was subcutaneously implated into the right axillary space of each of male ddY mice weighing $20 \pm 2$ g.

A test compound was dissolved in a physiological saline solution or a polyoxyethylene sorbitan monolaurate-containing physiological saline solution, and 0.1 to 0.2 ml of the solution was intravenously injected to five mice as one group 24 hours after the implatation of the tumor cells.

The anti-tumor activity of the test compound was determined by measuring the major diameter (a) and the minor diameter (b) of the tumor 7 days after the implantation of tumor cells, and the value of ($a \times b^2/2$), which corresponds to the volume of the tumor, was calculated. The intended anti-tumor activity is represented by a ratio of T/C, in which C indicates the tumor volume of mice of the control group to which a physiological saline solution instead of the test compound was administered and T indicates the tumor volume of mice of the test group to which the test compound was administered. T/C at each dose given was plotted in a graph in which T/C is shown by an ordinary scale on the vertical axis and a dose is shown by a logarithmic scale on the horizontal axis. The relation between the dose and T/C was determined to be a straight line by the least-squares method. From the regression formula of the straight line thus obtained, the dose of showing T/C=0.5 is calculated to give $ED_{50}$.

The results are shown in Table 3.

TABLE 3

| Test Compound | $ED_{50}$ (mg/Kg) |
| --- | --- |
| 2 | 3.7 |
| 3 | 8.9 |
| 11 | 5.9 |
| 13 | 36 |
| 16 | 24 |

Test Example 3

Actue Toxicity

A test compound was intravenously injected once to five ddY mice as one group. After the administration, the mice were observed for 14 days and deaths were noted. $LD_{50}$ was calculated from the death rate of each group according to the Behrens Kaerber's method.

The results are shown in Table 4.

TABLE 4

| Test Compound | $LD_{50}$ (mg/Kg) |
| --- | --- |
| 2 | 15 |
| 3 | 26 |
| 11 | 9.4 |
| 13 | >50 |
| 16 | 38 |

The compounds obtained by the present invention are useful as anti-tumor agents, which can be used directly as they are, or in various forms for administration. For instance, where Compounds (I) are used in the form of an injection, they are dissolved in a diluent which is conventionally used in the art, such as a physiological saline solution, or glucose, lactose or mannitol solution for injection. Alternatively, the compounds may be freeze-dried according to the Pharmacopoeia of Japan to give a powder for injection or may be prepared into injectable powder by adding sodium chloride thereto. In addition, the injection may also contain an auxiliary agent such as polyethylene glycol or HCO-60 (surfactant manufactured by Nikko Chemical Co.), as well as carriers such as ethanol and/or liposome or cyclodextrin. The injections are generally used for intravenous administration, but may also be used for intra-arterial administration, intraperitoneal administration or intra-thoracical administration.

Where the compounds of formula (I) are used as an oral drug, they may also be formed into tablets, granules, powder or syrup for oral administration with an appropriate excipient, disintegrator, binder or lubricant in a conventional manner. Further, Compounds (I) may be mixed with a conventionally used carrier and formed into suppositories for rectal administration in a conventional manner.

Dosage may appropriately vary according to the administration schedule, the kind of Compounds (I), and the age and condition of a patient. Administration schedule may also be varied according to the condition of a patient and the dosage. For example, the compounds can be intermittently administered in a dose of 0.06 to 6 mg/kg once a week or once every three weeks.

Certain embodiments of the invention are illustrated in the following examples.

Physicochemical data of each compound were obtained by using the following devices.

$^1$H-NMR: JEOL, Ltd. JMN-GX270 (270 MHz). VARIAN EM390 (90 MHz). Bruker AM400 (400 MHz).

MS: JEOL, Ltd. JSM-D300 (measured by the FAB or EI method).

IR: Nihon Bunko K. K., Japan IR-810 (measured by the KBr method).

TLC: silica gel Art 5715 (manufactured by Merck Inc.).

Preparative TLC: Silica gel Art 13794 (manufactured by Merck Inc.).

Example 1

Synthesis of 6-Demethyl-6-[(2-pyridylthio)methyl]mitomycin C (Compound 1)

416 mg of 1a-acetyl-7-demethoxy-6-demetyl-6,7-dihydro-7-ethylenedioxy-6-methylenemitomycin A (JP-A-70490/89 hereafter referred to as Compound "a") was dissolved in 30 ml of dichloromethane, and 112 mg of 2-mercaptopyridine was added to the solution. The mixture was stirred for 30 minutes at room temperature. The reaction mixture was washed with saturated aqueous sodium bicarbonate solution, phosphate buffer solution (pH 4) and saturated sodium chloride aqueous solution successively, and dried over anhydrous sodium sulfate. After the desiccant was filtered off, the solvent was distilled off under reduced pressure.

The residue obtained was purified by column chromatography (silica gel; chloroform:acetone = 1:1) to obtain red fractions and the solvent was distilled off. The residue obtained was dissolved in a small amount of chloroform, and n-hexane was added to the solution to give a powder. After the solvent was distilled off, the residue was dried thoroughly in vacuo to give 322 mg (yield 61%) of 1a-acetyl-7-demethoxy-6-methyl-6,7-dihydro-7-ethylenedioxy-6-[(2-pyridylthio)methyl]-mitomycin A (compound "a") as a red powder.

159 mg of Compound "a" was dissolved in 50 ml of methanol, and 500 mg of ammonium acetate was added to the solution. The reaction mixture was stirred for 22 hours at room temperature. Then, the solvent of the reaction mixture was distilled off, and the residue obtained was purified by column chromatography (silica gel; chloroform:methanol = from 30:1 to 20:1) to obtain purple fractions. The resultant solution was treated as described above to give 22.0 mg (yield 16%) of Compound 1 as a purple powder.

TLC: Rf 0.31 (chloroform:methanol = 9:1).

FAB-MS (m/z): 444 (M+ +1): $C_{20}H_{21}N_5O_5S$: 443.

IR ($cm^{-1}$): 3420, 3300, 3200, 2930, 1720, 1610, 1550, 1340, 1070.

$^1$H-NMR: δ, ppm (270 MHz, pyridine-$d_5$). 2.12 (bs, 1H), 2.74 (bs, 1H), 3.12 (bs, 1H), 3.18 (s, 3H), 3.57 (bd, J=13 Hz, 1H), 4.01 (dd, J=4.3 and 11.3 Hz, 1H), 4.50 (s, 2H), 4.56 (d, J=12.8 Hz, 1H), 5.09 (bt, J=11 Hz, 1H), 5.40 (dd, J=4.3 & 10.3 Hz, 1H), 6.91 (m, 1H), 7.2–7.25 (m, 1H), 7.37 (dt, J=1.9 and 7.8 Hz, 1H), 7.4–8.2 (br, 4H), 8.41 (bd, J=4.2 Hz, 1H)

Example 2

Synthesis of 6-Demethyl-6-[[(3-hydroxypyridin-2-yl)thio]methyl]-mitomycin C (Compound 2)

313 mg of Compound "a" was dissolved in 30 ml of dichloromethane, and 95 mg of 3-hydroxy-2-mercaptopyridine and 100 μl of triethylamine were added to the solution. The reaction mixture was stirred for 30 minutes at room temperature. The resultant reaction mixture was washed with phosphate buffer solution (pH 4), saturated aqueous sodium bicarbonate solution and saturated sodium chloride aqueous solution successively. The solution obtained was dried over anhydous sodium sulfate. After the desiccant was removed by filtration, the solvent was distilled off under reduced pressure.

The residue obtained was purified by column chromatography (silica gel; chloroform:methanol = 20:1) to obtain orange fractions. The solvent was distilled off and the residue obtained was treated in the same manner as described above to give 190 mg (yield 47%) of 1a-acetyl-7-demethoxy-6-demethyl-6,7-dihydro-7-ethylenedioxy-6-[[(3-hydroxypyridin-2-yl)thio]methyl]mitomycin A (Compound "b") as a red powder.

190 mg of Compound "b" was dissolved in 20 ml of anhydrous tetrahydrofuran, and the solution was allowed to stand for 49 hours at room temperature under dry ammonia atmosphere. Then the solvent was distilled off, and the resulting residue was purified by column chromatography (silica gel; chloroform:methanol = 20:1 to 10:1) to obtain purple fractions. The fractions thus obtained were treated in the same manner as described above to give 47.6 mg (yield 30%) of Compound 2 as a purple powder.

TLC: Rf 0.19 (chloroform:methanol = 9:1).

FAB-MS (m/z): 460 (M+ +1); $C_{20}H_{21}N_5O_6S$: 459.

IR ($cm^{-1}$): 3360, 3120, 2920, 2850, 1710, 1600, 1550, 1430, 1370, 1330, 1280, 1260, 1210, 1060.

$^1$H-NMR: δ, ppm (270 MHz, pyridine-$d_5$). 2.21 (bs, 1H), 2.79 (bs, 1H), 3.16 (bs, 1H), 3.23 (s, 3H), 3.64 (d, J=12.3 Hz, 1H), 4.05 (dd, J=4.3 and 11.1 Hz, 1H), 4.57 (d, J=12.8 Hz, 1H), 5.04 (bt, J=10 Hz, 1H), 5.41 (dd, J=4.4 and 10.4 Hz, 1H), 5.66 (d, J=14.5 Hz, 1H), 5.80 (d, J=14.5 Hz, 1H), 6.53 (dd, J=6.8 and 7.7 Hz ,1H), 7.00 (dd, J=1.3 and 7.7 Hz, 1H), 7.4–8.0 (bs, 2H), 7.91 (dd, J=1.1 and 6.6 Hz, 1H), 8.6–9.0 (bs, 2H), 9.33 (bs, 1H)

Example 3

Synthesis of 6-Demethyl-6-[(2-pyrimidinylthio)methyl]mitomycin C (Compound 3)

420 mg of Compound "a" was dissolved in dichloromethane, and 111 mg of 2-mercaptopyrimidine and 50 μl of triethylamine were added to the solution. The reaction mixture was stirred for 3 hours at room temperature. The resultant reaction mixture was washed with phosphate buffer solution (pH 4) and saturated sodium chloride aqueous solution successively. The solution was dried over anhydrons sodium sulfate. After the desiccant was removed by filtration, the solvent was distilled off under reduced pressure.

The residue obtained was purified by column chromatography (silica gel; chloroform:methanol = 25:1) to obtain orange fractions. The solvent was distilled off and the residue obtained was treated in the same manner as described in Example 1 to give 362 mg of 1a-acetyl-7-demethoxy-6-demethyl-6,7-dihydro-7-ethylenedioxy-6-[(2-pyrimidinylthio)methyl]mitomycin A (Compound "c") as a red powder.

362 mg of Compound "c" was dissolved in 50 ml of anhydrous tetrahydrofuran, and the solution was allowed to stand for 150 hours at room temperature under dry ammonia atmosphere. Then the solvent was distilled off, and the resulting residue was purified by column chromatography (silica gel; chloroform:methanol = 30:1 to 15:1) to obtain purple fractions. The fractions thus obtained were treated in the same manner as described in Example 1 to give 121 mg (yield 40%) of Compound 3 as a purple powder.

TLC: Rf 0.27 (chloroform:methanol = 9:1).

FAB-MS (m/z): 445 (M+ +1); $C_{19}H_{20}N_6O_5S$ = 444.

IR ($cm^{-1}$): 3400, 3330, 3180, 2930, 1710, 1600, 1570, 1550, 1460, 1440, 1380, 1340, 1200, 1070.

$^1$H-NMR: δ, ppm (270 MHz, pyridine-d$_5$). 1.9–2.4 (bs, 1H), 2.74 (bs, 1H), 3.13 (bs, 1H), 3.19 (s, 3H), 3.60 (bd, J=12 Hz, 1H), 4.03 (dd, J=4.2 and 11.2 Hz, 1H), 4.53 (s, 2H), 4.56 (d, J=12.8 Hz, 1H), 5.08 (t, J=10.4 Hz, 1H), 5.42 (dd, J=4.2 and 10.4 Hz, 1H), 6.85 (t, J=4.9 Hz, 1H), 7.4–7.9 (bs, 2H), 7.4–8.7 (br, 2H), 8.47 (d, J=4.8 Hz, 2H).

Example 4

Synthesis of 6-Demethyl-6-[[(4,6-dimethylpyrimidin-2-yl)thio]methyl]mitomycin C (Compound 4)

419 mg of Compound "a" was dissolved in 30 ml of dichloromethane, and 139 mg of 4,6-dimethyl-2-mercaptopyrimidine and 10 μl of triethylamine were added to the solution. The mixture was stirred for 2 hours and 15 minutes at room temperature. The reaction mixture was purified by column chromatography (silica gel; chloroform:methanol=50:1) to obtain orange fractions. The solvent was distilled off, and the residue obtained was treated in the same manner as described in Example 1 to give 383 mg (yield 69%) of 1a-acetyl-7-demethoxy-6-demethyl-6-[[(4,6-dimethylpyrimidin-2-yl)thio]methyl]-6,7-dihydro-7-ethylenedioxy mitomycin A (Compound "d") as a red powder.

383 mg of Compound "d" was dissolved in 50 ml of anhydrous tetrahydrofuran, and the solution was allowed to stand for 48 hours at room temperature under dry ammonia atmosphere. Then the solvent of the reaction mixture was distilled off, and the resulting residue was purified by column chromatography (silica gel; chloroform:methanol=30:1 to 20:1) to obtain purple fractions. The fractions thus obtained were treated in the same manner as described in Example 1 to give 200 mg (yield 62%) of Compound 4 as a purple powder.

TLC: Rf 0.28 (chloroform:methanol=9:1).

FAB-MS (m/z): 473 (M++1); $C_{21}H_{24}N_6O_5S=472$.

IR (cm$^{-1}$) 3380, 3200, 2950, 1720, 1610, 1580, 1550, 1440, 1340, 1270 1230, 1070.

$^1$H-NMR: δ, ppm (270 MHz, pyridine-d$_5$). 2.13 (bs, 1H), 2.26 (s, 6H), 2.74 (bs, 1H), 3.14 (bs, 1H), 3.18 (s, 3H), 3.57 (bd, J=12.6 Hz, 1H), 4.01 (dd, J=4.2 and 11.2 Hz, 1H), 4.49 (s, 2H), 4.56 (d, J=12.8 Hz, 1H), 5.09 (bt, J=10.8 Hz, 1H), 5.40 (dd, J=4.3 and 10.4 Hz, 1H), 6.52 (s, 1H), 7.4–7.9 (bs, 2H).

Example 5

Synthesis of 6-Demethyl-6-[(2-imidazolylthio)methyl]mitomycin C (Compound 5)

422 mg of Compound "a" was dissolved in 40 ml of dichloromethane, and 105 mg of 2-mercaptoimidazole and 50 μl of triethylamine were added to the solution. The mixture was stirred for 2 hours at room temperature. The resultant reaction mixture was washed with saturated sodium chloride aqueous solution, and the solution was dried over anhydrous sodium sulfate. After the desiccant was removed by filtration, the solvent was distilled off under reduced pressure.

The residue obtained was purified by column chromatography (silica gel; chloroform:methanol=20:1 to 10:1) to obtain yellow fractions. The solvent was distilled off and the residue obtained was treated in the same manner as described in Example 1 to give 146 mg (yield 28%) of 1a-acetly-7-demethoxy-6-demethyl-6,7-dihydro-7-ethylenedioxy-6-[(2-imidazolylthio)methyl]-mitomycin A (compound "e") as a red powder.

103 mg of Compound "e" was dissolved in 20 ml of anhydrous tetrahydrofuran, and the solution was allowed to stand for 191 hours at room temperature under dry ammonia atmosphere. Then the solvent of the reaction mixture was distilled off, and the resulting residue was purified by column chromatography (silica gel; chloroform:methanol=9:1) to obtain brown fractions. The fractions thus obtained were treated in a similar manner to Example 1 to give 60.6 mg (yield 70%) of Compound 5 as a brown powder.

TLC: Rf 0.20 (chloroform:methanol=9:1).

FAB-MS (m/z): 433 (M++1); $C_{18}H_{20}N_6O_5S=432$.

IR (cm$^{-1}$): 3370, 3200, 3020, 2940, 1720, 1710, 1610, 1570, 1550, 1540, 1460, 1340, 1070.

$^1$H-NHR: δ, ppm (270 MHz, pyridine-d$_5$). 2.09 (bs, 1H), 2.78 (dd, J=1.8 and 4.3 Hz, 1H), 3.14 (d, J=4.4 Hz, 1H), 3.21 (s, 3H), 3.65 (dd, J=1.8 and 12.7 Hz, 1H), 4.00 (dd, J=4.3 and 11.1 Hz, 1H), 4.60 (d, J=12.7 Hz, 1H), 5.03 (bt, J=11 Hz, 1H), 5.18 (d, J=14.4 Hz, 1H), 5.30 (d, J=14.4 Hz, 1H), 5.37 (dd, J=4.4 and 10.5 Hz, 1H), 6.70 (d, J=1.7 Hz, 1H), 7.14 (d, J=2.2 Hz, 1H), 7.3–7.8 (br, 2H), 8.40 (bs, 1H), 9.19 (bs, 1H), 14.0 (bs, 1H)

Example 6

Synthesis of 6-Demethyl-6-[[(1-methylimidazol-2-yl)thio]methyl]-mitomycin C (Compound 6)

331 mg of Compound "a" was dissolved in 40 ml of dichloromethane, and 94.6 mg of 2-mercapto-1-methylimidazole and 100 μl of triethylamine were added to the solution. The mixture was stirred for 3 hours and 15 minutes at room temperature. The resultant reaction mixture was washed with phosphate buffer solution (pH 4) and saturated sodium chloride aqueous solution successively, and the solution was dried over anhydrous sodium sulfate. After the desiccant was removed by filtration, the solvent was distilled off under reduced pressure.

The residue obtained was purified by column chromatography (silica gel; chloroform:methanol=30:1) to obtain yellow fractions. The solvent was distilled off and the residue obtained was treated in the same manner as described in Example 1 to give 224 mg (yield 58%) of 1a-acetyl-7-demethoxy-6-demethyl-6,7-dihydro-7-ethylenedioxy -6-[[(1-methylimidazol-2-yl)thio]methyl]-mitomycin A (Compound "f") as a yellow powder.

207 mg of Compound "f" was dissolved in 30 ml of anhydrous tetrahydroufuan, and the solution was allowed to stand for 232 hours at room temperature under dry ammonia atmosphere. Then the solvent in the reaction mixture was distilled off, and the resulting residue was purified by column chromatography (silica gel; chloroform:methanol=30:1) to obtain brown fractions. The fractions thus obtained were treated in the same manner as described in Example 1 to give 89.0 mg (yield 51%) of Compound 6 as a purple powder.

TLC: Rf 0.32 (chloroform:methanol=9:1).

FAB-MS (m/z): 448 (M++2); $C_{19}H_{22}N_6O_5S=446$.

IR (cm$^{-1}$): 3370, 3180, 2930, 1720, 1710, 1660, 1600, 1560, 1550, 1450, 1440, 1400, 1350, 1330, 1220, 1060.

$^1$H-NMR: δ, ppm (90 MHz, pyridine-d$_5$). 2.04 (s, 1H), 2.75 (bs, 1H), 3.10 (bs, 1H), 3.18 (s, 3H), 3.48 (s, 3H), 3.58 (dd, J=2 and 12 Hz, 1H), 3.94 (dd, J=4 and 10 Hz, 1H), 4.53 (d, J=12 Hz, 1H), 4.96 (bt, J=10 Hz, 1H), 5.11 (bs, 2H), 5.32 (dd, J=4 and 10 Hz, 1H), 6.76 (d, J=2 Hz, 1H), 6.99 (d, J=2 Hz, 1H), 7.3–7.6 (bs, 2H), 8.1–8.5 (bs, 1H), 8.5–9.0 (bs, 1H)

Example 7

Synthesis of 6-Demethyl-6-[[(1,2,4-triazol-3-yl)thio]methyl]mitomycin C (Compound 7)

420 mg of Compound "a" was dissolved in 40 ml of dichloromethane, and 110 mg of 3-mercapto-1,2,4-triazole was added to the solution. The reaction mixture was stirred for 4 hours at room temperature. The resultant reaction mixture was washed with saturated sodium chloride aqueous solution, and the reaction mixture was dried over anhydrous sodium sulfate successively. After the desiccant was removed by filtration, the solvent was distilled off under reduced pressure.

The resulting residue was purified by column chromatography (silica gel; chloroform:methanol=30:1) to obtain reddish purple fractions. The solvent in the fractions was distilled off and the residue obtained was treated in the same manner as described in Example 1 to give 77.2 mg (yield 15%) of 1a-acetly-7-demethoxy-6-demethyl-6,7-dihydro-7-ethylenedioxy-6-[[(1,2,4-triazol-3-yl)thio]methyl]mitomycin A (Compound "g") as a reddish purple powder.

52.2 mg of Compound "g" was dissolved in 20 ml of anhydrous tetrahydrofuran, and the solution was allowed to stand for 15 hours and 30 minutes at room temperature under dry ammonia atmosphere. The solvent in the reaction mixture was distilled off, and the resulting residue was purified by column chromatography (silica gel; chloroform:methanol=9:1) to obtain purple fractions. The fractions thus obtained were treated in the same manner as described in Example 1 to give 1.5 mg (yield 3.5%) of Compound 7 as a purple powder.

TLC: Rf 0.16 (chloroform:methanol=9:1).

FAB-MS (m/z): 434 (M++1); $C_{17}H_{19}N_7O_5S=433$.

IR (cm$^{-1}$): 3370, 3200, 3000, 2930, 1720, 1710, 1660, 1600, 1560, 1550, 1480, 1450, 1340, 1210, 1070.

$^1$H-NMR: δ, ppm (270 MHz, pyridine-d$_5$). 2.15 (bs, 1H), 2.79 (bs, 1H), 3.15 (bs, 1H), 3.22 (s, 3H), 3.63 (bd, J=12.8 Hz, 1H), 4.01 (dd, J=4.2 and 11.2 Hz, 1H), 4.55 (d, J=12.6 Hz, 1H), 5.06 (bt, J=10 Hz, 1H), 5.09 (d, J=14.5 Hz, 1H), 5.17 (d, J=14.5 Hz, 1H), 5.38 (dd, J=4.4 and 10.4 Hz, 1H), 7.4–7.8 (bs, 4H), 8.51 (s, 1H), 8.6–8.9 (br, 1H)

Example 8

Synthesis of 6-Demethyl-6-[[(4-methyl-1,2,4-triazol-3-yl)thio]methyl]mitomycin C (Compound 8)

421 mg of Compound "a" was dissolved in 40 ml of dichloromethane, and 116 mg of 3-mercapto-4-methyl-1,2,4-triazole and 100 μl of triethylamine were added to the solution. The reaction mixture was stirred for an hour and 45 minutes at room temperature. The resultant reaction mixture was washed with phosphate buffer solution (pH 4) and saturated sodium chloride aqueous solution successively. The solution was dried over anhydrous sodium sulfate. After the desiccant was removed by filtration, the solvent was distilled off under reduced pressure.

The residue obtained was purified by column chromatography (silica gel; chloroform:methanol=30:1) to obtain yellow fractions. The solvent in the fractions were distilled off and the residue obtained was treated in the same manner as described in Example 1 to give 196 mg (yield 37%) of 1a-acetyl-7-demethoxy-6-demethyl-6,7-dihydro-7-ethylenedioxy -6-[[(4-methyl-1,2,4-triazol-3-yl)thio]methyl]mitomycin A (Compound "h") as a yellow powder.

154 mg of Compound "h" was dissolved in 40 ml of anhydrous tetrahydrofuran, and the solution was allowed to stand for 327 hours at room temperature under dry ammonia atmosphere. Then the solvent of the reaction mixture was distilled off, and the residue obtained was purified by column chromatography (silica gel; chloroform:methanol=30:1) to obtain purple fractions. The fractions thus obtained were treated in the same manner as described in Example 1 to give 91.0 mg (yield 70%) of Compound 8 as a purple powder.

TLC: Rf 0.41 (chloroform:methanol=9:1).

FAB-MS (m/z): 449 (M++2); $C_{18}H_{21}N_7O_5S=447$

IR (cm$^{-1}$); 3350, 3130, 2920, 2850, 1720, 1710, 1600, 1570, 1550, 1540, 1450, 1340, 1210, 1060.

$^1$H-NMR: δ, ppm (90 MHz, pyridine-d$_5$). 1.96 (bs, 1H), 2.60 (m, 1H), 3.01 (m, 1H), 3.06 (s, 3H), 3.38 (s, 3H), 3.47 (bd, J=12 Hz, 1H), 3.87 (dd, J=4 and 11 Hz, 1H), 4.46 (d, J=12 Hz, 1H), 4.90 (bt, J=11 Hz, 1H), 5.13 (dd, J=4 and 11 Hz, 1H), 5.37 (s, 2H), 7.48 (bs, 2H), 8.13 (bs, 2H), 8.28 (s, 1H)

Example 9

Synthesis of 6-Demethyl-6-[[(1-methyltetrazol-5-yl)thio]methyl]-mitomycin C (Compound 9)

418 mg of Compound "a" was dissolved in 40 ml of dichloromethane, and 115 mg of 5-mercapto-1-methyltetrazole and 100 μl of triethylamine were added to the solution. The reaction mixture was stirred for an hour at room temperature. The resultant reaction mixture was washed with phosphate buffer solution (pH 4) and saturated sodium chloride aqueous solution successively. The solution was dried over anhydrous sodium sulfate. After the desiccant was removed by filtration, the solvent was distilled off under reduced pressure.

The residue obtained was purified by column chromatography (silica gel; chloroform:methanol=30:1) to obtain orange fractions. The solvent in the fractions was distilled off and the residue obtained was treated in the same manner as described in Example 1 to give 297 mg (yield 55%) of 1a-acetyl-7-demethoxy-6-demethyl-6,7-dihydro-7-ethylenedioxy-6-[[(1-methyltetrazol-5-yl)thio]methyl]mitomycin A (Compound "i") as a yellow powder.

277 mg of Compound "i" was dissolved in 40 ml of anhydrous tetrahydrofuran, and the solution was allowed to stand for 107 hours at room temperature under dry ammonia atmosphere. Then the solvent was distilled off, and the resulting residue was purified by preparative TLC (silica gel; chloroform:methanol=9:1) to obtain a purple zone. The zone was extracted with chloroform-methanol. After the solvent was distilled off, and the residue obtained was treated in the same manner as described in Example 1 to give 57.5 mg (yield 25%) of Compound 9 as a purple powder.

TLC: Rf 0.27 (chloroform:methanol=9:1).

FAB-MS (m/z) 437: (M++1); $C_{16}H_{20}N_8O_5S=436$.

IR (cm$^{-1}$): 3350, 3300, 3200, 2940, 1710, 1600, 1560, 1550, 1450, 1340, 1070.

$^1$H-NMR: δ, ppm (90 MHz, pyridine-d$_5$). 2.0 (bs, 1H), 2.63 (m, 1H), 3.03 (m, 1H), 3.10 (s, 3H), 3.49 (bd, J=13 Hz, 1H), 3.65 (s, 3H), 3.90 (dd, J=5 and 11 Hz, 1H), 4.46 (d, J=13 Hz, 1H), 4.93 (bt, J=11 Hz, 1H), 5.22 (dd, J=5 and 10 Hz, 1H), 5.34 (s, 2H), 7.3–7.6 (br, 2H), 8.0–8.5 (br, 2H)

Example 10

Synthesis of 6-Demethyl-6-[[(1-phenyltetrazol-5-yl)thio]methyl]-mitomycin C (Compound 10)

420 mg of Compound "a" was dissolved in 40 ml of dichloromethane, and 179 mg of 5-mercapto-1-phenyl-tetrazole and 100 μl of triethylamine were added to the solution. The reaction mixture was stirred for 4 hours and 10 minutes at room temperature. The resultant reaction mixture was washed with phosphate buffer solution (pH 4) and saturated sodium chloide aqueous solution successively. The solution was dried over anhydrous sodium sulfate. After the desiccant was removed by filtration, the solvent was distilled off under reduced pressure.

The residue obtained was purified by column chromatography (silica gel; chloroform:methanol=30:1 to 20:1) to obtain yellow fractions. The solvent in the fractions was distilled off and the residue obtained was treated in the same manner as described in Example 1 to give 320 mg (yield 53%) of 1a-acetyl-7-demethoxy-6-demethyl-6,7-dihydro-7-ethylenedioxy-6-[[(1-phenyl-tetrazol-5-yl)thio]methyl]mitomycin A (Compound "j") as a yellow powder.

304 mg of Compound "j" was dissolved in 40 ml of anhydrous tetrahydrofuran, and the solution was allowed to stand for 18 hours at room temperature under dry ammonia atmosphere. Then the solvent was distilled off, and the resulting residue was purified by preparative TLC (silica gel; chloroform:methanol=9:1) to give a purple zone. The zone was extracted with chloroform-methanol. After the solvent was distilled off, the residue obtained was treated in the same manner as descirbed in Example 1 to give 11.9 mg (yield 5%) of Compound 10 as a purple powder.

TLC: Rf 0.42 (chloroform:methanol=9:1).
FAB-MS (m/z): 512 (M++2); $C_{22}H_{22}N_8O_5S=510$.
IR (cm$^{-1}$): 3400, 3200, 2930, 1720, 1710, 1600, 1560, 1550, 1450, 1340, 1070.
$^1$H-NMR: δ, ppm (90 MHz, pyridine-d$_5$). 2.00 (bs, 1H), 2.56 (m, 1H), 3.04 (m, 1H), 3.12 (s, 3H), 3.52 (dd, J=2–13 Hz, 1H), 3.93 (dd, J=5 and 11 Hz, 1H), 4.48 (d, J=13 Hz, 1H), 4.96 (t, J=11 Hz, 1H), 5.30 (dd, J=5 and 11 Hz, 1H), 5.47 (s, 2H), 7.2–8.1 (m, 7H), 8.28 (bs, 2H)

Example 11

Synthesis of 6-Demethyl-6-[(2-thiazolinylthio)methyl]mitomycin C (Compound 11)

After 415 mg of Compound "a" was dissolved in 30 ml of dichloromethane and 120 mg of 2-mercaptothiazoline and 50 μl of triethylamine were added to the solution. The reaction mixture was stirred for 45 minutes at room temperature. The resultant reaction mixture was washed with saturated aqueous sodium bicarbonate solution, phosphate buffer solution (pH 4) and saturated sodium chloride aqueous solution successively. The solution was dried over anhydrous sodium sulfate. After the desiccant was removed by filtration, the solvent was distilled off under reduced pressure.

The residue obtained was purified by column chromatography (silica gel; chloroform:methanol=30:1 to 20:1) to obtain orange fractions. The solvent in the fractions was distilled off and the residue obtained was treated in the same manner as described in Example 1 to give 336 mg (yield 63%) of 1a-acetyl-7-demethoxy-6-demethyl-6,7-dihydro-7-ethylenedioxy-6-[(2-thiazolinylthio)methyl]mitomycin A (Compound "k") as a yellow powder.

336 mg of Compound "k" was dissolved in 30 ml of anhydrous tetrahydrofuran, and the solution was allowed to stand for 116 hours at room temperature under dry ammonia atmosphere. Then the solvent was distilled off, and the resulting residue was purified by column chromatography (silica gel; chloroform:methanol=20:1) to obtain purple fractions. The fractions thus obtained were treated in the same manner as described in Example 1 to give 188 mg (yield 67%) of Compound 11 as a purple powder.

TLC: Rf 0.29 (chloroform:methanol=9:1).
FAB-MS (m/z): 452 (M++1); $C_{18}H_{21}N_5O_5S_2=451$.
IR (cm$^{-1}$): 3380, 3200, 2940, 1720, 1710, 1600, 1570, 1550, 1540, 1450, 1340, 1320, 1220, 1060.
$^1$H-NMR; δ, ppm (270 MHz, pyridine-d$_5$). 2.21 (bs, 1H), 2.81 (bs, 1H), 3.04 (t, J=8.0 Hz, 2H), 3.15 (bs, 1H), 3.25 (s, 3H), 3.64 (bd, J=12.8 Hz, 1H), 3.96 (t, J=8.2 Hz, 2H), 4.03 (dd, J=4.2 and 11.2 Hz,1H), 4.58 (d, J=12.8 Hz, 1H), 4.81 (d, J=14.3 Hz, 1H), 5.09 (bt, J=11 Hz, 1H), 5.13 (d, J=ca.14 Hz, 1H), 5.39 (dd, J=4.1 and 10.5 Hz, 1H), 7.4–7.9 (bs, 2H), 7.8–8.0 (bs, 1H), 8.4–8.6 (bs, 1H)

Example 12

Synthesis of 6-Demethyl-6-[(2-thiazolylthio)methyl]mitomycin C (Compound 12)

416 mg of Compound "a" was dissolved in 30 ml of dichloromethane, and 116 mg of 2-mercaptothiazole and 50 μl of triethylamine were added to the solution. The reaction mixture was stirred for 2 hours and 10 minutes at room temperature. The resultant reaction mixture was directly purified by column chromatography (silica gel; chloroform: methanol=50:1 to 20:1) to obtain orange fractions. The solvent in the fractions was distilled off, and the resulting residue was treated in the same manner as described in Example 1 to give 335 mg (yield 63%) of 1a-acetyl-7-demethoxy -6-demethyl-6,7-dihydro-7-ethylenedioxy-6-[(2-thiazolylthio)methyl]-mitomycin A (Compound "m") as a yellow powder.

335 mg of Compound "m" was dissolved in 50 ml of anhyrous tetrahydrofuran, and the solution was allowed to stand for 72 hours at room temperature under dry ammonia atmosphere. Then the solvent was distilled off, and the resulting residue was purified by column chromatography (silica gel; chloroform:methanol=30:1 to 20:1) to obtain purple fractions. The solvent in the fractions was distilled off, and the residue thus obtained was treated in the same manner as described in Example 1 to give 177 mg (yield 63%) of Compound 12 as a purple powder.

TLC: Rf 0.31 (chloroform:methanol=9:1).
FAB-MS (m/z): 450 (M++1); $C_{18}H_{19}N_5O_5S_2=449$.
IR (cm$^{-1}$): 3370, 3200, 2930, 1720, 1600, 1570, 1550, 1450 1340, 1210, 1060.
$^1$H-NMR: δ, ppm (270 MHz, pyridine-d$_5$). 2.20 (bs, 1H), 2.80 (bs, 1H), 3.16 (bs, 1H), 3.23 (s, 3H), 3.63 (d, J=12.5 Hz, 1H), 4.02 (dd, J=4.2 and 11.2 Hz, 1H), 4.56 (d, J=12.8 Hz, 1H), 5.08 (bt, J=11 Hz, 1H), 5.18 (d, J=14.3 Hz, 1H), 5.30 (d, J=14.5 H), 1H), 5.38 (dd, J=4.4 and 10.4 Hz, 1H), 6.78 (d, J=4.6 Hz, 1H), 7.4–7.9 (bs, 2H), 7.51 (d, J=4.6 Hz, 1H), 8.4–8.7 (bs, 2H).

Example 13

Synthesis of 6-Demethyl-6-[(2-benzothiazolylthio)methyl]mitomycin C (Compound 13)

263 mg of Compound "a" was dissolved in 30 ml of dichloromethane, and 105 mg of 2-mercaptobenzothiazole and 100 μl of triethylamine were added to the solution. The reaction mixture was stirred for 4 hours at room temperature. The resultant reaction mixture was washed with phosphate buffer solution (pH 4) and saturated sodium chloride aqueous solution successively. The solution was dried over anhydrous sodium sulfate. After the desiccant was removed by filtration, the solvent was distilled off under reduced pressure.

The residue obtained was purified by column chromatography (silica gel; chloroform:methanol=30:1) to obtain yellow fractions. The solvent in the fractions was distilled off and the residue thus obtained was treated in the same manner as described in Example 1 to give 198 mg (yield 54%) of 1a-acetyl-6-[(2-benzothiazolylthio)methyl]-7 -demethoxy-6-demethyl-6,7-dihydro-7-ethylenedioxymitomycin A (Compound "n") as a yellow powder.

198 mg of Compound "n" was dissolved in 20 ml of anhydrous tetrahydrofuran, and the solution was allowed to stand for 41 hours at room temperature under dry ammonia atmosphere. Then the solvent was distilled off, and the resulting residue was purified by column chromatography (silica gel; chloroform:methanol=30:1) to give purple fractions. The fractions thus obtained were treated in the same manner as described in Example 1 to give 61.3 mg (yield 36%) of Compound 13 as a purple powder.

TLC: Rf 0.40 (chloroform:methanol=9:1).

FAB-MS: (m/z): 500 (M++1); $C_{22}H_{21}N_5O_5S_2=499$.

IR (cm$^{-1}$): 3450, 3370, 3150, 2950, 1720, 1600, 1560, 1550, 1540, 1460, 1330, 1060.

$^1$H-NMR: δ, ppm (90 MHz, pyridine-d$_5$). 2.19 (bs, 1H), 2.80 (bs, 1H), 3.16 (bs, 1H), 3.21 (s, 3H), 3.70 (bd, J=12.3 Hz, 1H), 4.00 (dd, J=4.2 and 11.2 Hz, 1H), 4.66 (d, J=12.8 Hz, 1H), 5.04 (bt, J=12 Hz, 1H), 5.36 (dd, J=4.0 and 10.4 Hz, 1H), 5.59 (d, J=15.0 Hz, 1H), 5.71 (d, J=15.0 Hz, 1H), 7.15–7.25 (m, 1H), 7.4–7.9 (br, 3H), 7.5–7.6 (m, 2H), 8.3–8.5 (bs, 1H), 8.62 (m, 1H)

Example 14

Synthesis of 6-Demethyl-6-[[(5-methyl-1,3,4-thiadiazol-2-yl)thio]methyl]mitomycin C (Compound 14)

430 mg of Compound "a" was dissolved in 40 ml of dichloromethane, and 136 mg of 2-mercapto-5-methyl-1,3,4-thiadiazole and 100 μl of triethylamine were added to the solution. The reaction mixture was stirred for one hour and 50 minutes at room temperature. The resultant reaction mixture was washed with phosphate buffer solution (pH 4) and saturated sodium chloride aqueous solution successively. The solution was dried over anhydrous sodium sulfate. After the desiccant was removed by filtration, the solvent was distilled off under reduced pressure.

The residue obtained was purified by column chromatography (silica gel; chloroform:methanol=30:1) to obtain orange fractions. The solvent in the fractions was distilled off and the residue thus obtained was treated in the same manner as described in Example 1 to give 448 mg (yield 79%) of 1a-acetyl-7-demethoxy-6-demethyl-6,7-dihydro-7-ethylenedioxy -6-[[(5-methyl-1,3,4-thiadiazol-2-yl)thio]methyl]mitomycin A (Compound "p") as a yellow powder.

428 mg of Compound "p" was dissolved in 40 ml of anhydrous tetrahydrofuran, and the solution was allowed to stand for 63 hours at room temperature under dry ammonia atmosphere. Then the solvent was distilled off, and the resulting residue was purified by column chromatography (silica gel; chloroform:methanol=30:1) to obtain purple fractions. The fractions thus obtained were treated in the same manner as described in Example 1 to give 176 mg (yield 49%) of Compound 14 as a purple powder.

TLC: Rf 0.28 (chloroform:methanol=9:1).

FAB-MS (m/z): 465 (M++1); $C_{18}H_{20}N_6O_5S_2=464$.

IR (cm$^{-1}$): 3400, 3300, 3200, 2920, 1720, 1600, 1560, 1550, 1340, 1210, 1060.

$^1$H-NMR: δ, ppm (270 MHz, pyridine-d$_5$). 2.12 (bs, 1H), 2.12 (s, 3H), 2.72 (bs, 1H), 3.13 (bs, 1H), 3 15 (s, 3H), 3.56 (bd, J=12.9 Hz, 1H), 4.00 (dd, J=4.3 and 11.1 Hz, 1H), 4.56 (d, J=12.7 Hz, 1H), 5.05 (bt, J=11 Hz, 1H), 5.37 (dd, J=4.2 and 10.5 Hz, 1H), 5.53 (s, 2H), 7.4–7.8 (br, 2H), 7.9–8.5 (br, 2H)

Example 15

Synthesis of 6-Demethyl-6-[(2-benzoxazolylthio)methyl]mitomycin C (Compound 15)

After 422 mg of Compound "a" was dissolved in 30 ml of dichloromethane, and 157 mg of 2-mercaptobenzoxazole and 50 μl of triethylamine were added to the solution. The reaction mixture was stirred for an hour and 40 minutes at room temperature. The resultant reaction mixture was washed with phosphate buffer solution (pH 4) and saturated sodium chloride aqueous solution successively. The reaction mixture was dried over anhydrous sodium sulfate. After the desiccant was removed by filtration, the solvent was distilled off under reduced pressure.

The residue obtained was purified by column chromatography (silica gel; chloroform:methanol=30:1) to obtain yellow fractions. The solvent in the fractions was distilled off and the residue obtained was treated in the same manner as described in Example 1 to give 393 mg (yield 68%) of 1a-acetyl-6-[(2-benzoxazolylthio)methyl]-7-demethoxy-6-demethyl-6,7-dihydro-7-ethylenedioxymitomycin A (Compound "r") as a yellow powder.

373 mg of Compound "r" was dissolved in 30 ml of anhydrous tetrahydrofuran, and the solution was allowed to stand for 22 hours at room temperature under dry ammonia atmosphere. Then the solvent in the reaction mixture was distilled off, and the resulting residue was purified by column chromatography (silica gel; chloroform:methanol=30:1 to 20:1) to obtain purple fractions. The fractions thus obtained were treated in the same manner as described in Example 1 to give 166 mg (yield 53%) of Compound 15 as a purple powder.

TLC: Rf 0.35 (chloroform:methanol=9:1).

FAB-MS (m/z): 484 (M++1); $C_{22}H_{21}N_5O_6S=483$.

IR (cm$^{-1}$): 3450, 3370, 3310, 3180, 2930, 1730, 1720, 1600, 1570, 1550, 1480, 1450, 1390, 1340, 1070.

$^1$H-NMR: δ, ppm (270 MHz, pyridine-d$_5$). 2.14 (bs, 1H), 2.78 (bs, 1H), 3.14 (bs, 1H), 3.21 (s, 3H), 3.67 (bd, J=12.8 Hz, 1H), 4.01 (dd, J=4.3 and 11.1 Hz, 1H), 4.61

(d, J=12.6 Hz, 1H), 5.04 (bt, J=9.7 Hz, 1H), 5.28 (bs, 2H), 5.37 (dd, J=4.1 and 10.5 Hz, 1H), 7.06-7.17 (m, 2H), 7.29-7.32 (m, 1H), 7.4-7.7 (bs, 2H), 7.81-7.85 (m, 1H), 8.1-8.4 (bs, 1H), 8.5-8.9 (bs, 1H).

Example 16

Synthesis of 6-Demethyl-6-[[(2,3,4,6-tetra-O-acetyl-$\beta$-D-glucopyranosyl)thio]methyl]mitomycin C (Compound 16)

After 215 mg of Compound "a" was dissolved in 20 ml of dichloromethane, and 195 mg of 1-thio-$\beta$-D-glucose tetraacetate and 50 $\mu$l of triethylamine were added to the solution. The reaction mixture was stirred for 3 hours and 50 minutes at room temperature. The resultant reaction mixture was washed with phosphate buffer solution (pH 4) and saturated sodium chloride aqueous solution successively. The reaction mixture was dried over anhydrous sodium sulfate. After the desiccant was removed by filtration, the solvent was distilled off under reduced pressure.

The residue obtained was purified by column chromatography (silica gel; chloroform:methanol=30:1) to obtain orange fractions. The solvent in the fractions was distilled off and the residue obtained was treated in the same manner as described in Example 1 to give 182 mg (yield 45%) of 1a-acetly-7-demethoxy-6-demethyl-6,7-dihydro-7-ethylenedioxy -6-[[(2,3,4,6-tetra-O-acetyl-8-D-glucopyranosyl)thio]-methyl]mitomycin A (Compound "s") as a yellow powder.

182 mg of Compound "s" was dissolved in 30 ml of anhydrous tetrahydrofuran, and the solution was allowed to stand for 187 hours at room temperature under dry ammonia atmosphere. Then the solvent was distilled off, and the resulting residue was purified by column chromatography (silica gel; chloroform:methanol=30:1) to obtain purple fractions. The fractions thus obtained were treated in the same manner as described in Example 1 to give 98.1 mg (yield 60%) of Compound 16 as a purple powder.

TCL: Rf 0.36 (chloroform:methanol=9:1).

FAB-MS (m/z): 697 (M++1); $C_{29}H_{36}N_4O_{14}S=696$.

IR (cm$^{-1}$): 3430, 3330, 3200, 2940, 1750, 1600, 1550, 1430, 1370, 1340, 1230, 1040.

$^1$H-NMR: $\delta$, ppm (270 MHz, pyridine-d$_5$). 1.9-2.2 (bs, 1H), 1.99 (s, 3Hx2), 2.01 (s, 3Hx2), 2.75 (bs, 1H), 3.12 (bs, 1H), 3.24 (s, 3H), 3.60 (d, J=12.8 Hz, 1H), 4.02 (d, J=13.9 Hz, 1H), 4.02 (dd, J=3.9 and 10.8 Hz, 1H), 4.13 (ddd, J=2.6 and 4.8 and 10.1 Hz, 1H), 4.22 (d, J=13.2 Hz, 1H), 4.40 (dd, J=2.3 and 12.4 Hz, 1H), 4.58 (dd, J=4.9 and 12.6 Hz, 1H), 4.59 (d, J=12.8 Hz, 1H), 5.03 (m, 1H), 5.23 (d, J=10.1 Hz, 1H), 5.38 (dd, J=4.3 and 10.5 Hz, 1H), 5.52 (t, J=9.5 Hz, 1H), 5.58 (t, J=9.5 Hz, 1H), 5.74 (t, J=9.2 Hz, 1H), 7.3-7.8 (bs, 2H), 7.95 (bs, 2H)

Example 17

Synthesis of 6-Demethyl-6-[($\beta$-D -glucopyranosylthio)methyl]mitomycin C (Compound 17)

24.7 mg of Compound 16 obtained in Example 16 was dissolved in 6.1N ammonia-methanol solution, and the reaction mixture was allowed to stand in a sealed reaction vessel for 10 hours and 30 minutes at room temperature. The solvent in the reaction mixture was distilled off and the resulting residue was purified by reverse phase short column chromatography (Bond Elute C18; elution, water:acetonitrile=100:0 to 60:40) to give purple fractions. The organic solvent in the fractions was distilled off under reduced pressure and the resulting aqueous solution was freeze-dried to give 14.8 mg (yield 79%) of Compound 17 as purple amorphous solids.

FAB-MS (m/z): 530 (M++2); $C_{21}H_{28}N_4O_{10}S=528$.

IR (cm$^{-1}$): 3400, 3320, 2920, 1710, 1600, 1560, 1550, 1530, 1450, 1340, 1070.

$^1$H-NMR: $\delta$, ppm (270 MHz, pyridine-d$_5$). [Major peaks]2.01 (bs, 1H), 2.70 (bs, 1H), 3.09 (bs, 1H), 3.14 (s, 3H), 3.55 (bd, J=12 Hz, 1H), 3.9-4.2 (m, 6H), 4.21 (d, J=13.4 Hz, 1H), 4.29 (dd, 6.8 and 11.5 Hz, 1H), 4.53 (d, J=12.6 Hz, 1H), 4.60 (bd, J=10.1 Hz, 1H), 5.04 (bt, J=11 Hz, 1H), 5.11 (d, J=9.2 Hz, 1H), 5.33 (dd, J=4.0 and 10.4 Hz, 1H), 6.60 (bs, 1H), 7.11 (bs, 1H), 7.3-7.7 bs, 2H), 7.78 (bs, 2H)

Example 18

Synthesis of 6-Demethyl-6-[(2-thienylthio)methyl]mitomycin C (Compound 18)

430 mg of Compound "a" was dissolved in 40 ml of dichloromethane, and 100 $\mu$l of 2-mercaptothiophene and 100 $\mu$l of triethylamine were added to the solution. The reaction mixture was stirred for one hour and 20 minutes at room temperature.

The resultant reaction mixture was washed with phosphate buffer solution (pH 4) and saturated sodium chloride aqueous solution successively. The solution was dried over anhydrous sodium sulfate. After the desiccant was removed by filtration, the solvent was distilled off under reduced pressure.

The residue obtained was purified by column chromatography (silica gel; chloroform:methanol=30:1) to give red fractions. The solvent in the fractions was distilled off and the residue obtained was treated in the same manner as described in Example 1 to give 189 mg (yield 34%) of 1a-acetly-7-demethoxy-6-demethyl-6,7-dihyro-7-ethylenedioxy -6-[(2-thienylthio)methyl]mitomycin A (Compound "t") as a red powder.

176 mg of Compound "t" thus obtained above was dissolved in 40 ml of anhyrous tetrahydrofuran, and the solution was allowed to stand for 163 hours at room temperature under dry ammonia atmopshere. Then, the solvent of the reaction mixture was distilled off, and the resulting residue was purified by column chromatography (silica gel; chloroform:methanol=20:1) and then further purified by preparative TLC (chloroform:methanol=9:1) to give a purple zone. The zone was extracted and treated in the same manner as described in Example 9 to give 47.5 mg (yield 32%) of Compound 18 as a purple powder.

TLC: Rf 0.40 (chloroform:methanol=9:1).

FAB-MS (m/z): 449 (M++1); $C_{19}C_{20}N_4O_5S_2=448$.

IR (cm$^{-1}$): 3400, 3320, 3270, 3200, 1720, 1710, 1600, 1560, 1550, 1440, 1340, 1220, 1070.

$^1$H-NMR: $\delta$, ppm (270 MHz, pyridine-d$_5$). 1.9-2.2 (br, 1H), 2.72 (bs, 1H), 3.12 (bs, 1H), 3.19 (s, 3H), 3.54 (bd, J=ca. 13 Hz, 1H), 4.01 (dd, J=4.3 and 11.1 Hz, 1H), 4.25 (s, 2H), 4.42 (d, J=12.7 Hz, 1H), 5.02 (bt, J=ca. 11 Hz, 1H), 5.39 (dd, J=4.3 and 10.4 Hz, 1H), 6.91 (dd, J=3.7 and 5.4 Hz, 1H), 7.15-7.25 (m, overlapped with pyridine, 1H), 7.38 (dd, J=1.2 and 5.4 Hz, 1H), 7.4-7.7 (br, 2H), 8.0-8.3 (br, 2H)

What is claimed is:

1. A mitomycin derivative represented by the Formula (I):

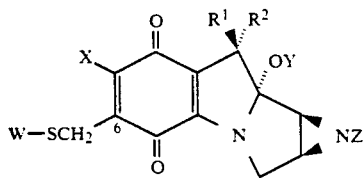 (I)

where W represents a member selected from the group consisting of (a), (b), (c), (d) and (e):

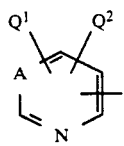 (a)

wherein A is —N= or —CR$^3$= wherein R$^3$ is selected from hydrogen, hydroxy, amino, phenyl and C1-6 alkyl, each of Q$^1$ and Q$^2$ are independently selected from hydrogen, hydroxy, amino, phenyl and C1-6 alkyl,

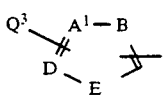 (b)

wherein A$^1$ has the same meaning as A, Q$^3$ has the same meaning as Q$^1$, B and D are each independently selected from —N= and —CR$^4$= wherein R$^4$ has the same meaning as R$^3$ with the proviso that when A$^1$, B and D are all —N=, then E is NR$^5$, E is selected from S, O and NR$^5$ wherein R$^5$ has the same meaning as R$^3$,

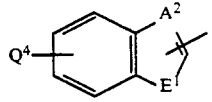 (c)

wherein A$^2$ has the same meaning as A, E$^1$ has the same meaning as E and Q$^4$ has the same meaning as Q$^1$,

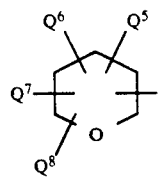 (d)

wherein Q$^5$, Q$^6$, Q$^7$ and Q$^8$ are each independently selected from hydrogen, hydroxy, C1-6 alkanoyloxy, hydroxymethyl and C1-6 alkanoyloxymethyl, and

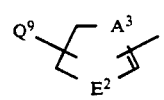 (e)

wherein A$^3$ has the same meaning as A, E$^2$ has the same meaning as E, Q$^9$ has the same meaning as Q$^1$, X is selected from methoxy and amino, Y is selected from hydrogen and methyl, Z is selected from hydrogen, methyl and C1-6 alkanoyl, and one of R$^1$ and R$^2$ represents carbamoyloxymethyl, and the other represents hydrogen or R$^1$ and R$^2$ are combined to form methylene.

2. The mitomycin derivative according to claim 1, wherein R$^1$ is arbamoyloxymethyl;

R$^2$ is hydrogen;

X is amino;

Y is methyl;

and Z is hydrogen.

3. The mitomycin derivative according to claim 2, wherein (a): represents

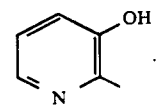

4. The mitomycin derivative according to claim 3, wherein one of Q$^1$ and Q$^2$ is hydrogen, the other is selected from hydrogen, hydroxy and C1-6 alkyl.

5. The mitomycin derivative according to claim 4, wherein W represents

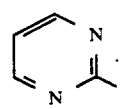

6. The mitomycin derivative according to claim 4, wherein W represents

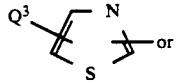

7. The mitomycin derivative according to claim 2, wherein (b): represents

8. The mitomycin derivative according to claim 7, wherein R$^5$ is selected from hydrogen, phenyl and C1-6 alkyl, and Q$^3$ is selected from hydrogen, hydroxy and C1-6 alkyl.

9. The mitomycin derivative according to claim 8, wherein W represents

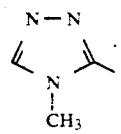

10. The mitomycin derivative according to claim 8, wherein W represents

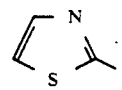

11. The mitomycin derivative according to claim 8, wherein W represents

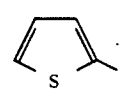

12. The mitomycin derivative according to claim 2, wherein (c): represents

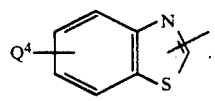

13. The mitomycin derivative according to claim 12, wherein $Q^4$ is selected from hydrogen, hydroxy and C1-6 alkyl.

14. The mitomycin derivative according to claim 13, wherein W represents

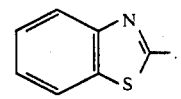

15. The mitomycin derivative according to claim 2, wherein $Q^5$, $Q^6$, $Q^7$ and $Q^8$ in the (d) group are each independently selected from C1-6 alkanoyloxy and C1-6 alkanoyloxymethyl.

16. The mitomycin derivative according to claim 15, wherein W represents

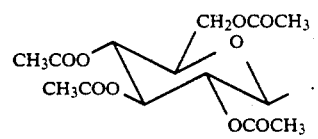

17. The mitomycin derivative according to claim 2, wherein (e): represents

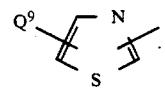

18. The mitomycin derivative according to claim 17, wherein $Q^9$ is selected from hydrogen, hydroxy and C1-6 alkyl.

19. The mitomycin derivative according to claim 18, wherein W represents

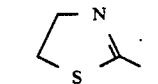

* * * * *